United States Patent [19]

Brizuela

[11] Patent Number: 5,197,956
[45] Date of Patent: Mar. 30, 1993

[54] PROTECTING DEVICE FOR GUIDE TUBES USED WITH BLOOD AND SERUM BAGS AND THE LIKE

[76] Inventor: Ricardo A. Brizuela, Diagonal 76 No 27, La Plata, Argentina

[21] Appl. No.: 413,952
[22] Filed: Sep. 28, 1989
[51] Int. Cl.⁵ .............................................. A61M 5/00
[52] U.S. Cl. ................................... 604/171; 604/198; 604/263
[58] Field of Search ............................ 604/162–163, 604/171, 192, 198, 263, 160, 411–414

[56] References Cited

U.S. PATENT DOCUMENTS

| | | | |
|---|---|---|---|
| 3,154,080 | 10/1964 | Rowan et al. | 604/171 |
| 4,693,708 | 9/1987 | Wanderer et al. | 604/263 |
| 4,731,059 | 3/1988 | Wanderer et al. | 604/198 |
| 4,762,516 | 8/1988 | Luther et al. | 604/198 |
| 4,778,453 | 10/1988 | Lopez | 604/198 |
| 4,846,804 | 7/1989 | Davis et al. | 604/263 |
| 4,846,811 | 7/1989 | Vanderhoof | 604/198 |
| 4,874,384 | 10/1989 | Nunez | 604/198 |
| 4,878,762 | 11/1989 | Uddo, Jr. et al. | 604/171 |
| 4,921,479 | 5/1990 | Grayzel | 604/160 |
| 4,931,048 | 6/1990 | Lopez | 604/198 |
| 4,943,283 | 7/1990 | Hogan | 604/412 |
| 4,955,866 | 9/1990 | Corey | 604/198 |

Primary Examiner—Stephen C. Pellegrino
Assistant Examiner—Michael Rafa
Attorney, Agent, or Firm—Darby & Darby

[57] ABSTRACT

Disclosed herein is a slidable protective sheath for use with needles that are attached to plastic guide tubes, i.e., the tubes attached to blood or serum bags. The slidable sheath protects the operator from injury from the needle when the needle is not in use. When the needle is in use, the sheath is moved along the guide tube away from the needle.

8 Claims, 3 Drawing Sheets

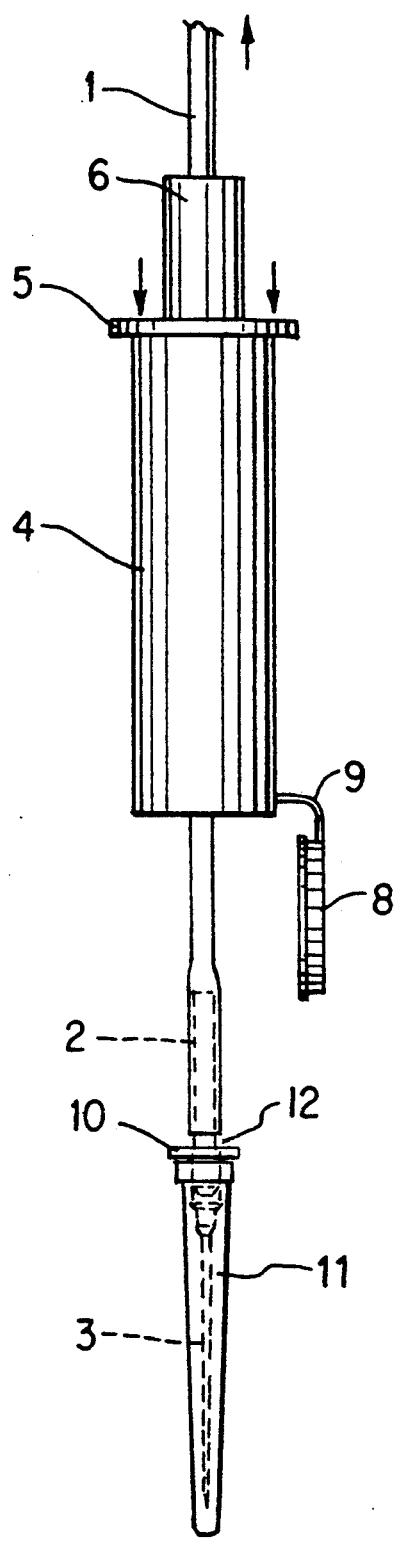
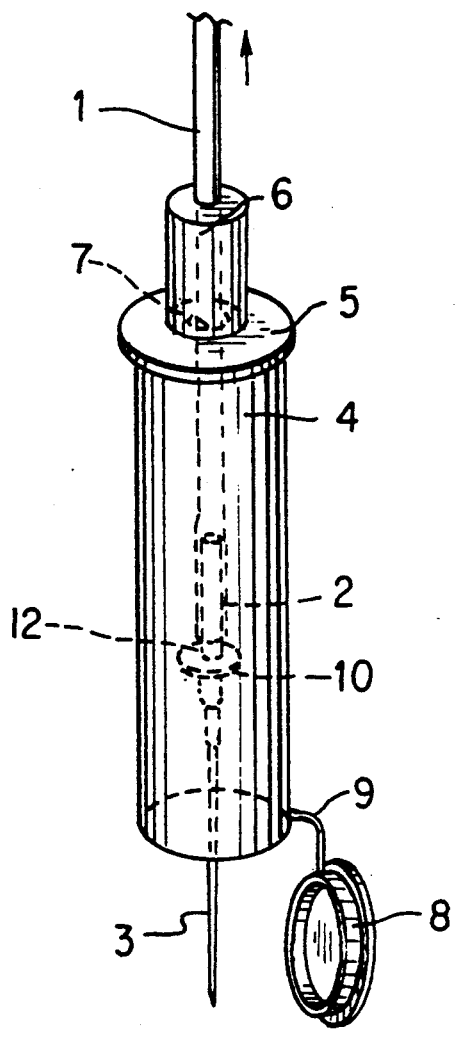
Fig. 1
Fig. 2

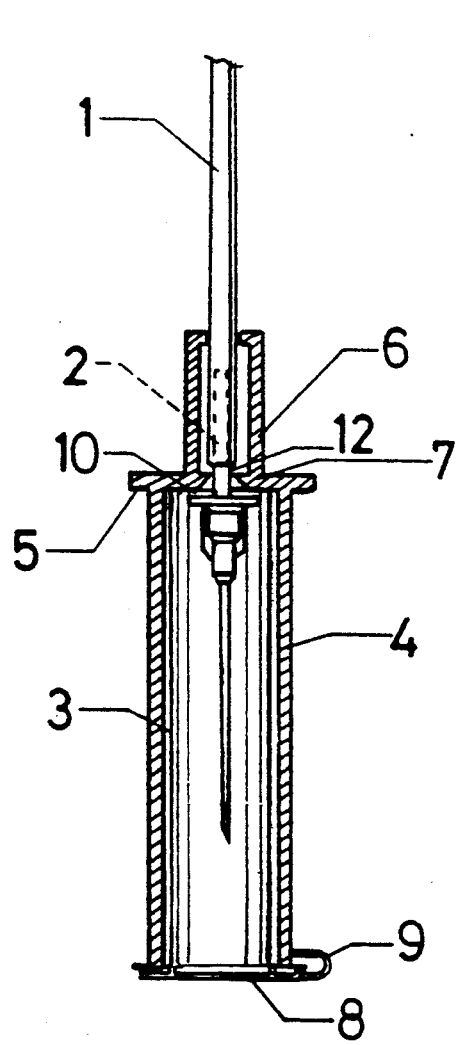
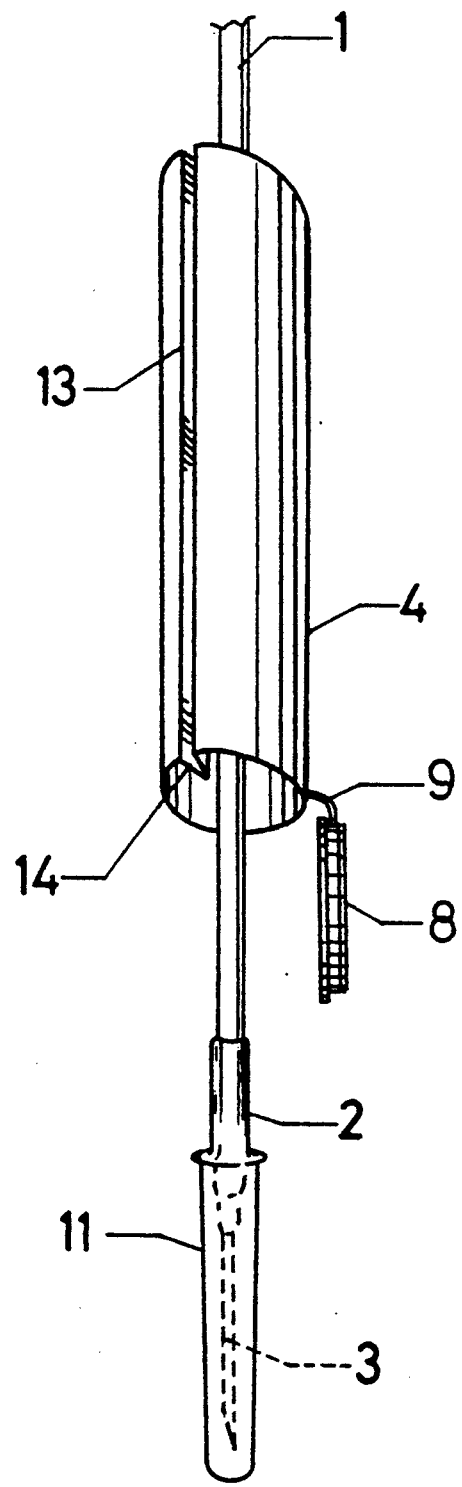
Fig. 3
Fig. 4

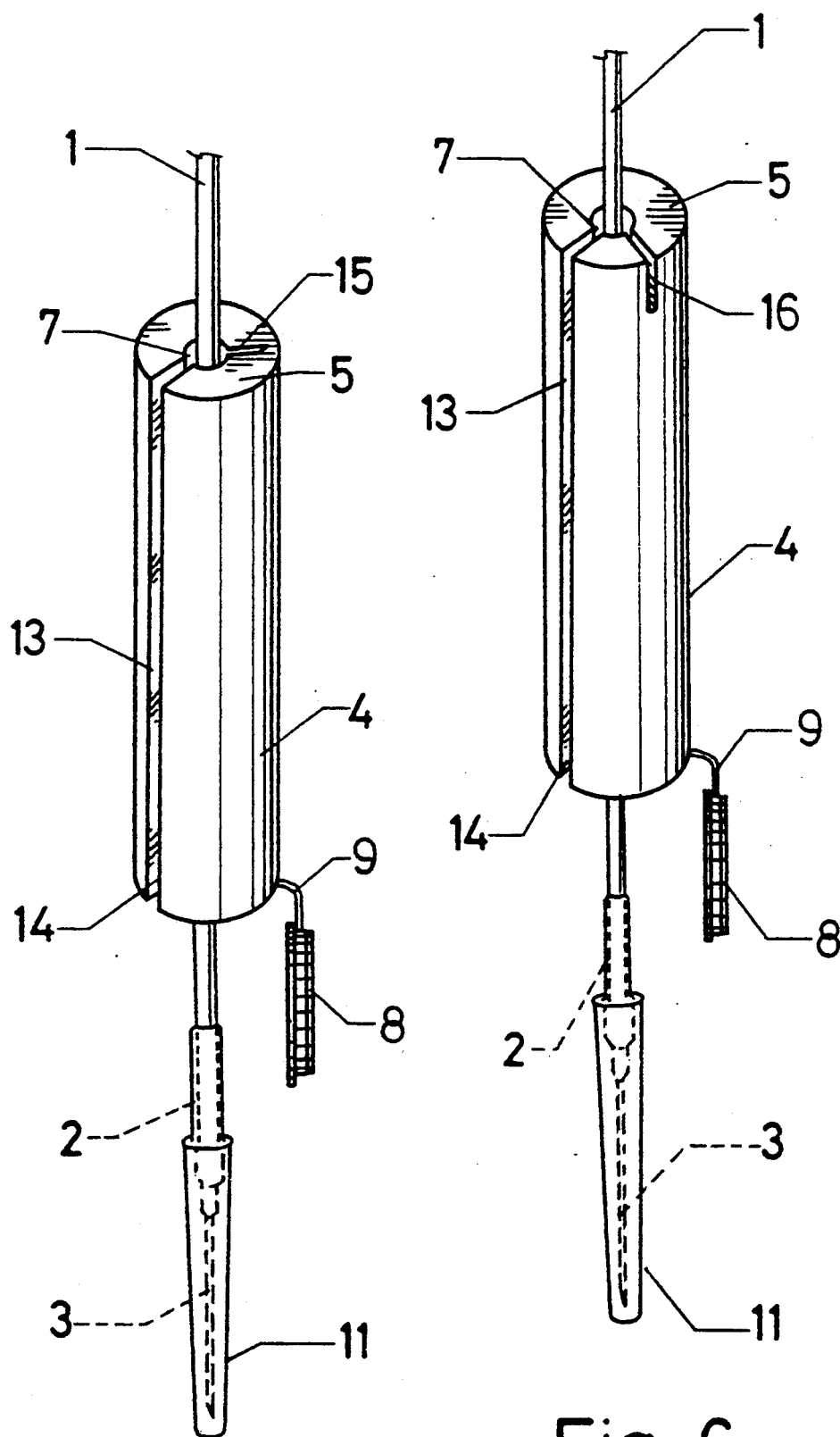

PROTECTING DEVICE FOR GUIDE TUBES USED WITH BLOOD AND SERUM BAGS AND THE LIKE

FIELD OF THE INVENTION

The present invention is related to devices generally used in medicine and, specifically, to a protecting device for guide tubes used in blood and serum bags; the main purpose thereof being to offer a useful device which allows the use of such blood or serum bags with no risk.

BACKGROUND OF THE INVENTION

Due to the nature of guide tube needles, their handling has always presented a certain risk, since needles are so sharp that they may cause injury.

For these reasons, physicians and nurses are extremely careful when using said needles in order to reduce the risk of injury and needle contamination. Consequently, withdrawing of the protecting capsule or sheath is done just before its use; the sheath consisting of a container with an open end and lengthened so as to keep the needle therein.

Although this protective sheath allows safe handling just before the patient is injected, it becomes useless when the needle is withdrawn. This is due to the fact that sometimes the needle is kept applied to the patient for a long time and, consequently, the sheath may be lost. It is also possible that the patient may have the guide tube applied in one location and be moved to another place, such as X-ray room, operating room, parturition room, therapy room, etc., with the sheath left at the former place.

Even when a protecting capsule is used, handling the capsule is rather difficult due to its small diameter which makes it easy to fail the intent of introducing the needle inside the sheath. Consequently, the person using it may be hurt by the contaminated needle.

The present invention deals with a protecting device for guide tubes used the device blood and serum bags and the like which provides permanent protection to the user or person handling same. The needle operates between two limit positions therein: the first one corresponding to the operative use of the needle and the other to the protected inoperative state of same.

Therefore it is clear that the protection provided to the needle by the sheath is complete not only for the operators, but also for cleaners, clerks and rubbish collectors.

Therefore, the utility of this invention is evident due to its novel features since it is suitable with any kind of waste guide tubes (serum, blood, etc.).

SUMMARY OF THE INVENTION

The present invention relates to a needle protecting device for guide tubes used with blood and serum bags and the like comprising a hollow cylindrical body, cylindrically arranged about a plastic tube connecting a blood or serum bag to the needle, wherein the length of the body is greater than that of the needle to be protected. The cylindrical body is slidably mounted on the plastic tube, the first end of the cylindrical body distal from the needle is closed by a fixed cap while the second end of same is open. The fixed cap has a hole parallel with the longitudinal axis through which the tube is insertably mounted. The edge of this hole has a means of hindering the needle from sliding along the plastic tube passing through the hole; the cylindrical body has a cap that is hingably connected to the body by a tongue piece such that it can close the open second end of the device.

BRIEF DESCRIPTION OF THE DRAWINGS

The present device is shown in the attached drawings, wherein:

FIG. 1: is a side view of the guide tube where the needle is inserted together with the needle protecting capsule or hood and the device of the invention is in such a position so as to allow the needle to operate;

FIG. 2: is a perspective view where the guide tube and needle may be observed, with the present device having been slid towards the needle;

FIG. 3: is a longitudinal section showing the needle inside the device after using the guide tube;

FIG. 4: is a perspective view of a variant of the protecting device showing the needle inserted together with the protecting capsule and with the device in an upper position regarding the needle;

FIG. 5: is a perspective view of another variant of the device; and

FIG. 6: is a perspective view showing a further variant of said device.

In these figures, same reference numbers indicate same or equivalent parts or elements of the device.

From a general point of view, guide tubes for blood or serum bags comprise a plastic tube (1), one of which ends is prolonged in a terminal part (2) where the needle (3) is assembled, connecting the inner part of the plastic tube outside, while the other end is connected to the flask or bag (not represented) containing blood, serum or the like.

The protecting device of this invention, as shown in FIGS. 1 to 3, comprises a hollow cylindrical body (4) mounted in a sliding way on the plastic tube (1). This cylindrical body is made of plastic material, preferably transparent, and is capable of keeping the needle inside when the body has been slid towards the end of the needle.

The upper end of the body (4) is closed by a fixed cap (5), while the lower end is opened.

Said fixed cap (5) has at the centre thereof a hollow cylindrical projection axially arranged with the longitudinal axis of the cylindrical body (4). Coincidentally with the axis of said body (4) there is a hole (7), the edge of which is bevelled, and through which the plastic tube (1) passes.

The open lower end of the body (4) may be closed by a cap (8), which is attached to said body by means of a tongue piece (9) acting as a hinge.

When using the device, and according to FIG. 1, the needle (3) is attached to the end of the plastic tube (1) having a circular rebound (10), the device being above said needle. Just before being applied to a patient, the protecting hood (11) is withdrawn and the needle applied to the body of the patient. After use, the needle is withdrawn from the patient and the sliding device of this invention moved until a circular slot (12) of the plastic tube (1) overlaps the bevelled edge of the hole (7) of the fixed cap (5). Thus, the combined actions of the circular rebound (10), circular slot (12) and bevelled edge of the hole (7), hinder the needle to slide or go backwards avoiding any kind of accident or contamination. The device with the needle inside is closed with the cap (8).

From the above disclosure it is evident that the protecting device of the invention is mounted on the plastic tube, forming a single unit.

However, there is a possibility of the protecting device being incorporated to the plastic tube at any moment during its use. This can be done by means of the variants shown in FIGS. 4 to 6.

According to these figures, the hollow cylindrical body (4) has a longitudinal slot (13) with lips (14) along its length, which allows said cylindrical body to be mounted on the plastic tube (1), as shown in said FIGS. 4 to 6, when necessary; the operation and use thereof being the same explained in connection with the embodiment of FIGS. 1 to 3.

In the variants exemplified by FIGS. 4 to 6, the cylindrical projection (6) is omitted and a longitudinal slot (13) is prolonged in the fixed cap (5) beyond the hole (7), the edge of which is not bevelled (see FIGS. 5 and 6). The extension of the longitudinal slot (13) may be as shown in (15) (FIG. 5) and (16) (FIG. 6). The operator may narrow the diameter of the plastic tube (1) by placing the latter in said slots by pressure, thus avoiding the possibility of the body sliding, consequently, avoiding a accident or contamination. Likewise, the slots 15 and 16 may completely restrain the passage of blood, serum or the like by the interior of the plastic tube (1), thus preventing leakage of the liquid when the tube is not used.

The diameter of the body (4) may vary in accordance with the features of the needle to be protected since, for instance, in connection with needles which are needles with two flexible, plastic fins that facilitate their use, it is necessary employ a body diameter greater than that corresponding to a protecting device for a standard needle.

I claim:

1. A fluid transferring assembly comprising:
   a hollow needle;
   a plastic tube connected at one end to said needle;
   a fluid container connected to the other end of said tube; and
   a needle protecting device comprising
      a hollow cylindrical body wherein said body is slidably mounted about said tube, said body is longer than said needle and has a first end distal to said needle and a second open end proximate to said needle and said body has a longitudinal open slot wherein the width of said longitudinal slot is narrower than the diameter of said tube,
      a fixed first cap covering said first end wherein said first cap has a hole through which said tube is mounted, said hole is coaxial with the axis of said body and said first cap has a first open cap slot connecting said longitudinal slot to said hole, said longitudinal and first slots allowing said device to be attached on said tube by inserting said tube through the longitudinal slot and first slot, and
      a second cap hinged to said body by a tongue piece such that said second cap can close the open end of the device and enclose said needle.

2. An assembly according to claim 1, wherein said protecting device comprises a transparent plastic material.

3. The assembly according to claim 1 wherein each side of said longitudinal slot has lips along its length such that said lips must be deformed to allow passage of said tube through said longitudinal slot.

4. A needle protecting device for a guide tube used with blood and serum bags comprising
   a hollow cylindrical body capable of being slidably mounted about a plastic tube wherein said body is longer than the length of said needle to be protected and has a first end and an open second end and said body has an longitudinal open slot wherein the width of said longitudinal slot is narrower than the diameter of said tube,
   a fixed first cap covering said first end wherein said first cap has a hole through which said tube is mounted, said hole is co-axial with the axis of said cylindrical body and said first cap has a first open cap slot connecting said longitudinal slot to said hole, whereby said longitudinal and first slots allow said device to be attached on said tube by inserting said tube through the longitudinal and first slot, and
   a second cap hinged to said body by a tongue piece to enable said second cap to close the open end of said body.

5. A needle protecting device according to claim 4 comprising a transparent plastic material.

6. The needle protecting device according to claim 4 wherein each side of said longitudinal slot has lips along its length such that said lips must be deformed to allow passage of said tube through said longitudinal slot.

7. A fluid transferring assembly comprising a hollow needle;
   a plastic tube connected at one end to said needle;
   a fluid container connected to the other end of said tube; and
   a needle protecting device comprising
      a hollow cylindrical body wherein said body is slidably mounted about said tube, said body is longer than said needle and has a first end distal to said needle and a second open end proximate to said needle and said body has a longitudinal open slot wherein the width of said longitudinal slot is narrower than the diameter of said tube,
      a fixed first cap covering said first end wherein said first cap has a hole through which said tube is mounted, said hole is co-axial with the axis of said body wherein said first cap has a first open cap slot connecting said longitudinal slot to said hole, said longitudinal and first slots allowing said device to be attached on said tube by inserting said tube through the longitudinal slot and first slot and said first cap has a second open slot, said second open slot is narrower than said tube such that said tube resists sliding when said tube is inserted into said second slot, and
      a second cap hinged to said body by a tongue piece such that said second cap can close the open end of the device and enclose said needle.

8. A needle protecting device for a guide tube used with blood and serum bags comprising
   a hollow cylindrical body capable of being slidably mounted about a plastic tube wherein said body is longer than the length of said needle to be protected and has a first end and an open second end and said body has an longitudinal open slot wherein the width of said longitudinal slot is narrower than the diameter of said tube,
   a fixed first cap covering said first end wherein said first cap has a hole through which said tube is mounted, said hole is co-axial with the axis of said cylindrical body wherein said first cap has a first open cap slot connecting said longitudinal slot to said hole, whereby said longitudinal and first slots allow said device to be attached on said tube by inserting said tube through the longitudinal and first slot, and said first cap has a second open slot, said second open slot is narrower than said tube such that said tube resists sliding when said tube is inserted into said second slot, and a second cap hinged to said body by a tongue piece to enable said second cap to close the open end of said body.

* * * * *